United States Patent
Mahmoud

(10) Patent No.: US 11,925,414 B2
(45) Date of Patent: Mar. 12, 2024

(54) OPTICAL TRIAL FRAME

(71) Applicant: OES Limited, Auckland (NZ)

(72) Inventor: Ryan Mahmoud, Auckland (NZ)

(73) Assignee: OES LIMITED, Auckland (NZ)

( * ) Notice: Subject to any disclaimer, the term of this patent is extended or adjusted under 35 U.S.C. 154(b) by 546 days.

(21) Appl. No.: 17/231,441

(22) Filed: Apr. 15, 2021

(65) Prior Publication Data

US 2021/0338078 A1 Nov. 4, 2021

(30) Foreign Application Priority Data

May 4, 2020 (AU) ............................... 2020202945

(51) Int. Cl.
| | | |
|---|---|---|
| *A61B 3/107* | (2006.01) | |
| *A61B 3/00* | (2006.01) | |
| *A61B 3/04* | (2006.01) | |
| *A61B 3/11* | (2006.01) | |
| *G02C 13/00* | (2006.01) | |

(52) U.S. Cl.
CPC ............ *A61B 3/107* (2013.01); *A61B 3/0008* (2013.01); *A61B 3/0041* (2013.01); *A61B 3/04* (2013.01); *A61B 3/111* (2013.01); *G02C 13/005* (2013.01)

(58) Field of Classification Search
CPC ......... A61B 3/0041; A61B 3/008; A61B 3/04; A61B 3/107; A61B 3/111; G02C 13/003; G02C 13/005; G01D 5/2412
See application file for complete search history.

(56) References Cited

U.S. PATENT DOCUMENTS

| | | |
|---|---|---|
| 8,220,923 B2 | 7/2012 | Saffra |
| 2014/0176909 A1 | 6/2014 | Spivey et al. |
| 2017/0188812 A1 | 7/2017 | Feiertag |

FOREIGN PATENT DOCUMENTS

| | | | |
|---|---|---|---|
| DE | 102017105366 A1 * | 9/2017 | |
| EP | 567817 A1 * | 11/1993 | ............ A61B 3/111 |
| GB | 2332062 A | 6/1999 | |
| WO | WO 2018/172366 A1 | 9/2018 | |

OTHER PUBLICATIONS

Australian Government, IP Australia, Examination Report No. 1, Application No. 2020202945, dated Jul. 28, 2020, six pages.

* cited by examiner

*Primary Examiner* — Jack Dinh
(74) *Attorney, Agent, or Firm* — WTA Patents

(57) ABSTRACT

Embodiments relate to an optical trial frame that includes: left and right frames extending in the left and right directions respectively; a bridge located between and connected to the left and right frames such that the left and right frames can move relative to each other along a longitudinal axis of the bridge; left and right temples connected to the respective left and right frames; left and right lens holders rotatably coupled to the left and right frames respectively and configured to receive and retain lenses in use; and, capacitive sensing means configured to detect and measure at least one of: a lateral position of one of the frames; and, a rotational position of one of the lens holders.

20 Claims, 4 Drawing Sheets

OPTICAL TRIAL FRAME

CROSS-REFERENCE TO RELATED APPLICATION

This application claims priority to Australian Patent Application No. 2020202945, filed on May 4, 2020, which is incorporated by reference herein in its entirety.

TECHNICAL FIELD

The present invention generally relates to optometry and ophthalmology, more particularly to an optical trial frame.

BACKGROUND

Subjective refraction is an attempt to determine, by trial and error using a patient's cooperation, the combination of ophthalmic lenses that will provide the Best Corrected Visual Acuity (BCVA). It is an examination used by orthoptists, optometrists and ophthalmologists to determine a patient's need for retractive correction, in the form of glasses or contact lenses. The aim is to improve current unaided vision or vision with current glasses.

In practice, a trial frame is typically adjusted to a patient and easily exchangeable insert lenses or trial lenses are inserted into the trial frame. The insert lenses are arranged in a rotatable manner so as to be able to correct astigmatic defects in their axial position. Lateral defects and height defects also need to be corrected and therefore the trial frame has to be precisely adjusted to the patient. To do so, trial frames are provided with different mechanisms allowing the orthoptists, optometrists or ophthalmologists to adjust a pupil distance of the trial frame and/or a height of the trial frame via a nose rest or pad and/or a length of temples of the trial frame and/or an angular position of cylinders/lenses of the trial frame. By pivoting the nose rest or pad and adjusting the length of the temples, a distance of the trial frame in relation to the eyes can be adjusted. For adjustment to different ear shapes, the temples may be configured to be pivotable in height and laterally.

Since the orthoptists, optometrists or ophthalmologists typically adjust the trial frame immediately on the head of the patient, the different adjustment mechanisms of the trial frame have to be easy to operate and they need to be arranged in a manner that allows ergonomic handling. At the same time, the different adjustment mechanisms need to allow the orthoptists, optometrists or ophthalmologists to perform accurate measurements, while enabling quick and easy visualization of these measurements.

However, most of the conventional trial frames merely comprise printed scales provided on different parts of the frame and require the orthoptists, optometrists or ophthalmologists to bend over to read these scales which are usually are hard to see. There is therefore a need for improved trial frames overcoming these drawbacks such that prescription values and/or measurements obtained from the different adjustment mechanisms can be easily obtained and read.

SUMMARY OF THE INVENTION

According to a first aspect of the disclosure there is provided a trial frame comprising: left and right frames extending in the left and right directions respectively; a bridge located between and connected to the left and right frames such that the left and right frames can move relative to each other along a longitudinal axis of the bridge; left and right temples connected to the respective left and right frames; left and right lens holders rotatably coupled to the left and right frames respectively and configured to receive and retain lenses in use; and, capacitive sensing means configured to detect and measure at least one of: a lateral position of one of the frames; and, a rotational position of one of the lens holders.

The capacitive sensing means may be configured to detect and measure linear motions of the left and right frames and/or rotational motions of the left and right lens holders.

The capacitive sensing means may comprise a first capacitive sensor configured to detect and measure a linear motion of at least one of the frames relative to the other and/or relative to the trial frame, the first capacitive sensor comprising: a fixed electrode coupled to one of the frames; and, a linear moving electrode configured to be electrically connected to the fixed electrode. The first capacitive sensor may be configured to detect and measure the linear motion with a minimum resolution of about. 0.5 degree. The first capacitive sensor may be configured to detect and measure a maximum linear motion of about 5 millimeters per second.

The capacitive sensing means may comprise one or more second capacitive sensors configured to detect and measure a rotational motion of lens holders relative to their respective frame, each of the one or more second capacitive sensors comprising: a fixed electrode coupled to one of the frames; and, a rotational moving electrode configured to be electrically connected to the fixed electrode. The second capacitive sensor may be configured to detect and measure a rotational motion with a minimum resolution of about 1 degree. The second capacitive sensor may be configured to detect and measure a maximum rotational motion of about 30 degrees per second.

The fixed electrodes may be formed as a conductive surface coupled to a printed circuit board. The linear moving electrode may be formed by a conductive surface of the bridge. The rotational moving electrode may be formed by a conductive surface coupled to the lens holders.

The capacitive sensing means may be configured to detect and measure a capacitance and/or a variation of capacitance when provided with an electrical charge.

The trial frame may comprise light sources arranged on the left and right frames and configured to illuminate in use a corneal apex of a user and/or a centre of pupils of a user. The light sources may comprise light-emitting diodes.

The trial frame may comprise a computing processing unit (CPU) configured to receive the measured lateral and rotational positions from the sensing means and to process the lateral positions to compute an interpupillary distance. The trial frame may be associated with one or more display units configured to display at least one of: the measured lateral position of at least one of the frames; the measured rotational position of one of at least one of the lens holders; and, the computed interpupillary distance. The at least one of the one or more display units may be integral with the left or right frame. The at least one of the one or more display units may be external to the trial frame. The trial frame may further comprise a transmitter configured to transmit the measured positions and/or the computed interpupillary distance to an external device and/or the at least one external display device.

The trial frame may further comprise one or more power supplies configured to provide power to at least the sensing means. The one or more power supplies may be configured to provide power to the CPU and/or the one or more display units.

The trial frame may further comprise a port configured to connect the trial frame to an external device. The external device may be a power source configured to recharge the one or more power supplies when connected to the trial frame. The external device may be configured to exchange data with the sensing means and/or the CPU when connected to the trial frame. The trial frame may further comprise a memory configured to store computer-executable instructions and/or data and wherein the external device may be configured to update the computer-executable instructions and/or data stored in the memory when connected to the trial frame.

According to a second aspect of the disclosure there is provided a trial frame comprising: left and right frames extending in the left and right directions respectively; a bridge located between and connected to the left and right frames such that the left and right frames can move relative to each other along a longitudinal axis of the bridge; left and right temples connected to the respective left and right frames; left and right lens holders rotatably coupled to the left and right frames respectively and configured to receive and retain lenses in use; and, light sources arranged on the left and right frames and configured to illuminate in use a corneal apex of a user and/or a centre of pupils of a user.

The light sources may comprise light-emitting diodes.

The trial frame may further comprise capacitive sensing means configured to detect and measure at least one of: a lateral position of one of the frames; and, a rotational position of one of the lens holders. The capacitive sensing means may comprise capacitive sensing means as any one of the examples and embodiments of the first aspect.

The trial frame may comprise one or more of: a computing processing unit (CPU) configured to receive the measured lateral and rotational positions from the sensing means and to process the lateral positions to compute an interpupillary distance; one or more display units configured to display at least one of: the measured lateral position of at least one of the frames; the measured rotational position of one of at least one of the lens holders; and, the computed interpupillary distance; a transmitter configured to transmit the measured positions and/or the computed interpupillary distance to an external device and/or the at least one external display device; one or more power supplies configured to provide power to at least the sensing means; a port configured to connect the trial frame to an external device; and, a memory configured to store computer-executable instructions and/or data.

The at least one of the one or more display units may be integral with the left or right frame and/or may be external to the trial frame.

The one or more power supplies may be configured to provide power to the CPU and/or the one or more display units.

The external device may be at least one or more of: a power source configured to recharge the one or more power supplies when connected to the trial frame; and, a device configured to exchange data with the sensing means and/or the CPU when connected to the trial frame.

To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting.

BRIEF DESCRIPTION OF THE DRAWINGS

Embodiments will now be described with reference to the accompanying drawings in which.

DESCRIPTION OF EMBODIMENTS

Figure 1:
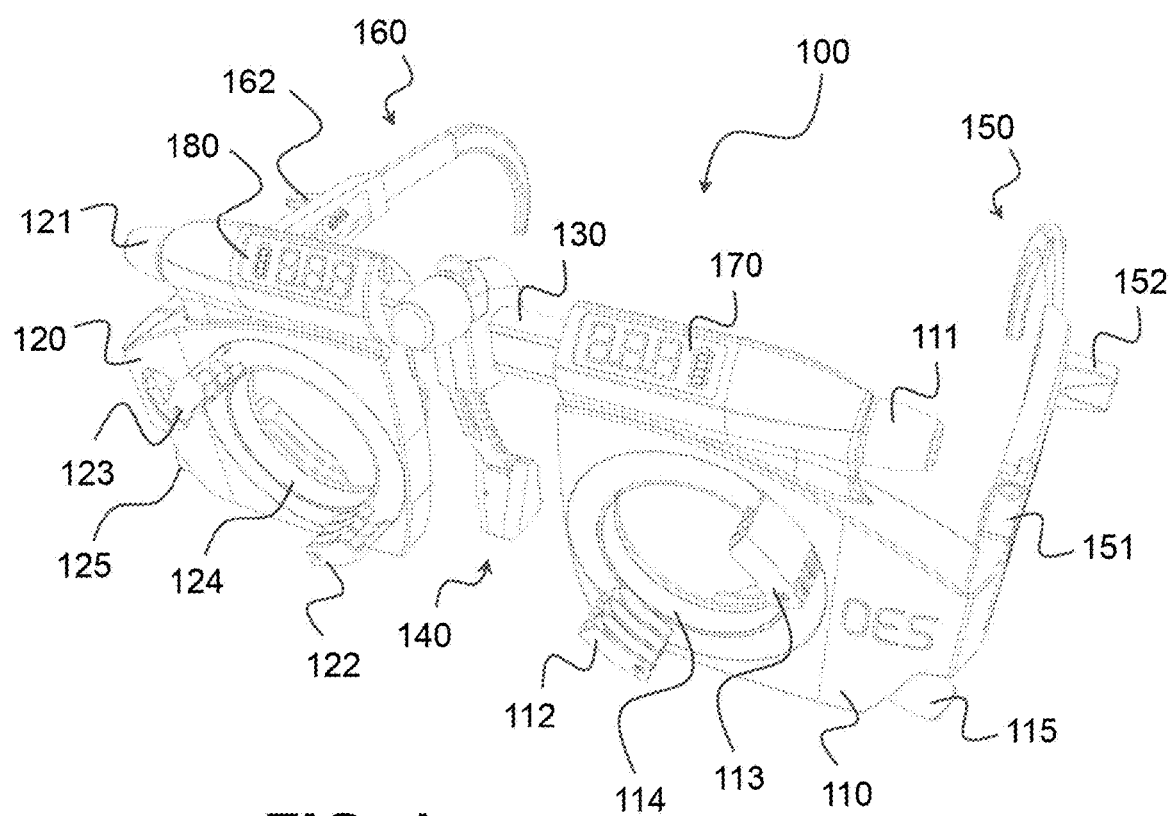
FIG. 1 is a perspective view of an optical trial frame constructed and operative in accordance with an embodiment of the invention.
Figure 2:
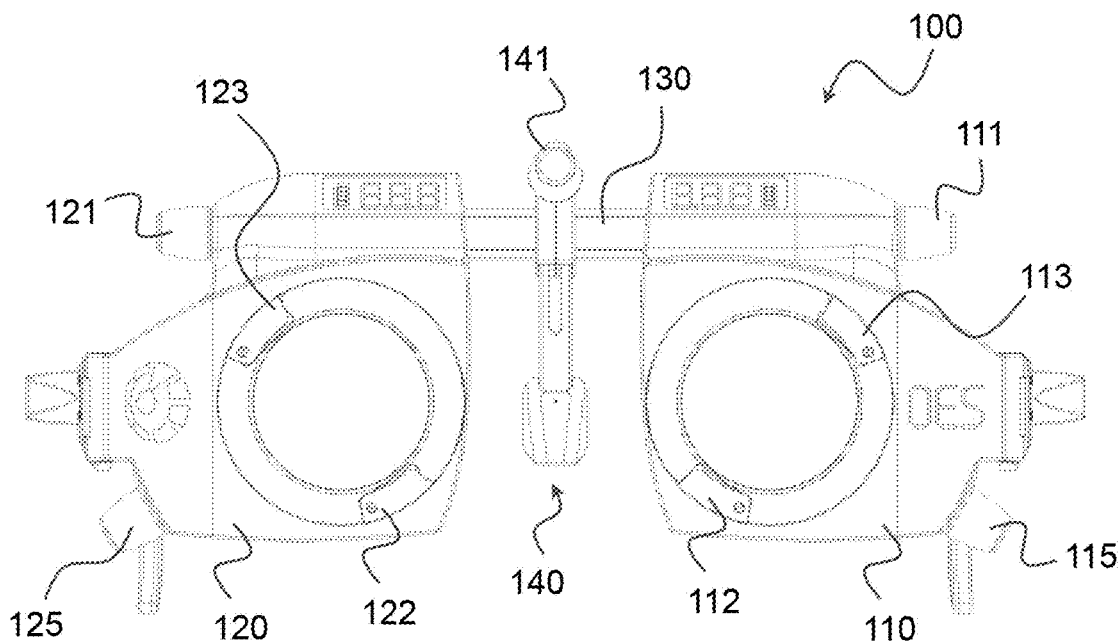
FIG. 2 is a front view of the optical trial frame of FIG. 1.
Figure 3:
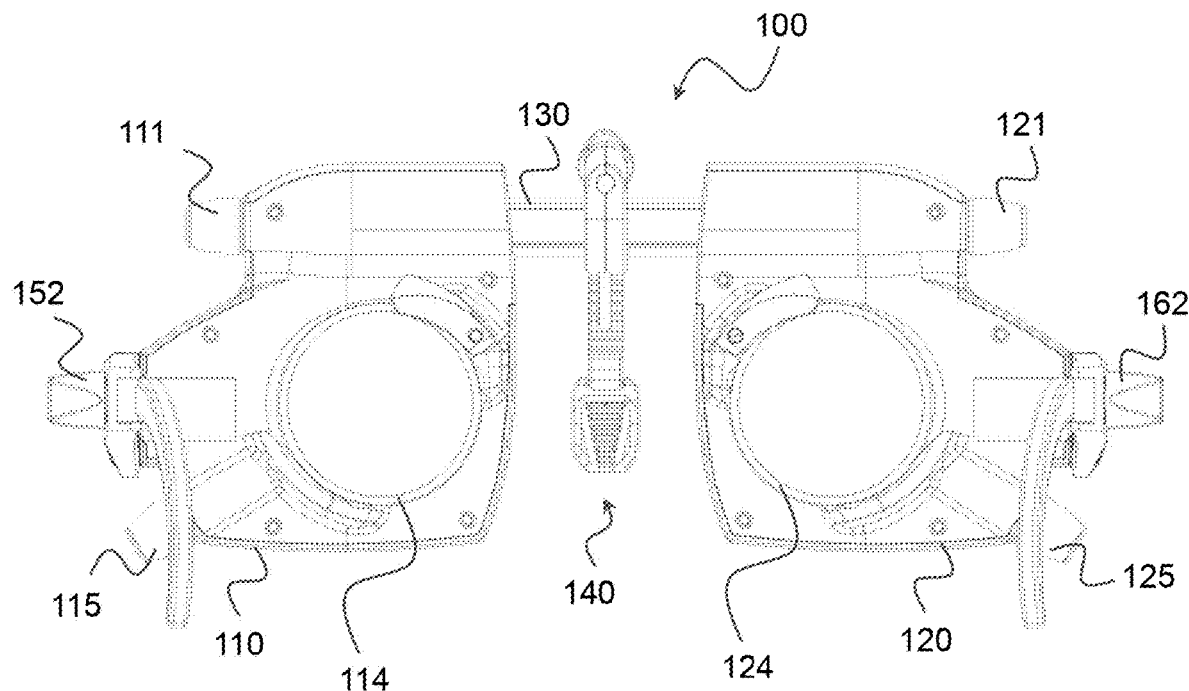
FIG. 3 is a rear view of the optical trial frame of FIG. 1.
Figure 4:
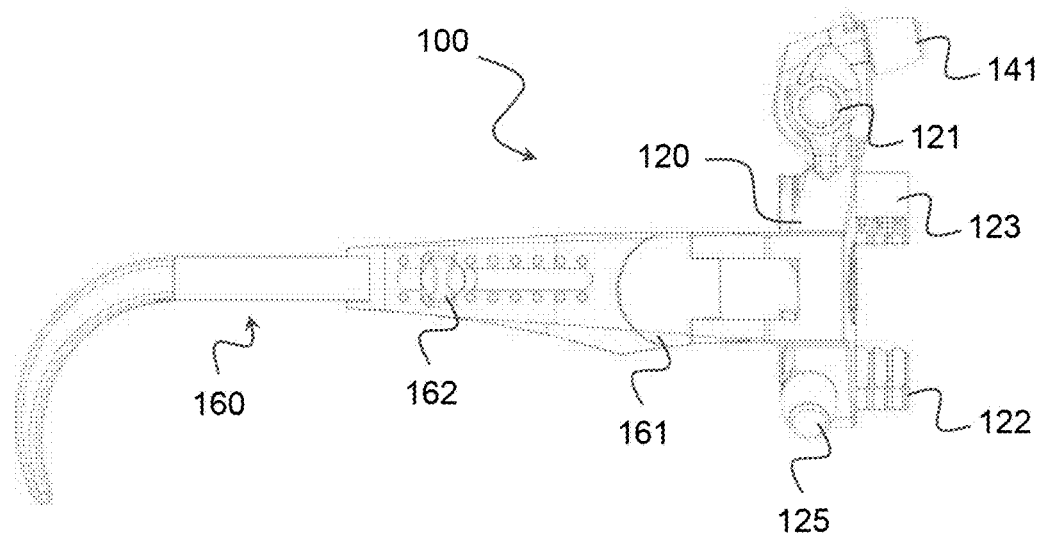
FIG. 4 is a side view of the optical trial frame of FIG. 1.

In the following description, several specific details are presented to provide a thorough understanding of the embodiments of the present invention. One skilled in the relevant art will recognize, however, that the present invention can be practiced without one or more of the specific details, or in combination with or with other components, etc. In other instances, well-known implementations or operations are not shown or described in detail to avoid obscuring aspects of various embodiments of the present invention.

The terms used in this specification generally have their ordinary meanings in the art and in the specific context where each term is used. The use of examples anywhere in this specification, including examples of any terms discussed herein, is illustrative only, and in no way limits the scope and meaning of the invention or of any exemplified term. Likewise, the present invention is not limited to various embodiments given in this specification.

As used herein, the terms "comprising," "including," "having," "containing," "involving," and the like are to be understood to be open-ended, i.e., to mean including but not limited to.

Reference throughout the specification to "one embodiment" or "an embodiment" means that a particular feature, structure, implementation, or characteristic described in connection with the embodiment is included in at least one embodiment of the present invention. Thus, uses of the phrases "in one embodiment" or "in an embodiment" in various places throughout the specification are not necessarily all referring to the same embodiment. Furthermore, the particular features, structures, implementation, or characteristics may be combined in any suitable manner in one or more embodiments.

FIGS. 1 to 4 illustrate different views of a trial frame constructed and operative in accordance with embodiments of the invention. The trial frame 100 is configured to determine a subjective refraction, i.e., a combination of ophthalmic lenses that will provide the BCVA of a patient. The trial frame 100 comprises left and right frames 110, 120, a bridge 130, a nose rest or pad 140, and left and right temples 150, 160. The trial frame 100 may further comprise sensing means and one or more display units 170, 180.

The left and right frames 110, 120 are connected to the bridge 130 in such a way that they can move relative to each other and/or relative to a longitudinal axis of the bridge 130. One or more operational elements 111, 121 such as, but not limited to, conical, cylindrical or frustoconical knobs are provided on an upper portion of the left and right frames 110, 120 adjacent the bridge 130 to allow lateral adjustment of the frames 110, 120 relative to the bridge 130. For example, the frames 110, 120 may be slidably mounted onto the bridge 130 and manual operation (e.g., rotation) of the operation elements 111, 121 moves the respective frames 110, 120 along the longitudinal axis of the bridge 130. Various mechanisms may be provided to allow displacement of the frames 110, 120 relative to the bridge 130 via the operational elements 111, 121. Such mechanisms and/or arrangements will be apparent to those skilled in the art and will not be detailed hereinafter. The positions of the two frames 110, 120 can therefore be adjusted laterally to place the center of respective lenses—received into and positioned in use within lens holders 112, 113, 122, 123—laterally in line with the patient's pupils. A lateral displacement (i.e., displacement along the longitudinal axis of the bridge 130) of the frames 110, 120 may therefore be detected and measured by the sensing means so as to determine lateral positions of the frames 110, 120 relative to each other and/or to the bridge 130. The positions of the frames 110, 120 can then be displayed on the one or more display units 170, 180. In addition, or alternatively, an interpupillary distance (PD) can be calculated using the sensed positions of the frames 110, 120 and displayed on the one or more displays 170, 180.

The nose pad 140 is connected to or mounted onto the bridge 130 and disposed between the left and right frames 110, 120. The nose pad 140 may be adapted to be coupled to the bridge 130 at a first end and may comprise a cushion or pad adapted to rest in use on a patient's nose at a second end opposite and/or distal to the first end. The nose pad 140 may be a nosepiece assembly comprising a plurality of parts which provide for the location of the trial frame 100 on the patient. The nose pad 140 may be adjusted in two ways. For example, the nose pad 140 can be configured to move fore and aft, so as to adjust a distance of the trial lenses—positioned in use within the lens holders 112, 113, 122, 123 of frames 110, 120—from the eye of the patient to meet the standard distance or the special distance chosen for the patient. The nose pad 140 may further be configured to move up and down, so as to place the centers of the lenses vertically in line with the patient's pupils. One or more operational elements 141 may be provided to allow adjustment of the nose pad 140 relative to the bridge 130. For example, an adjustment gear (shown in FIG. 5) can be provided to convert a rotational adjusting motion of knob 141 into a translational motion of the nose pad 140. Others mechanisms or arrangements to adjust the nose pad 140 relative to the trial frame 100 will be apparent to those skilled in the art and will not be detailed hereinafter.

Figure 5:
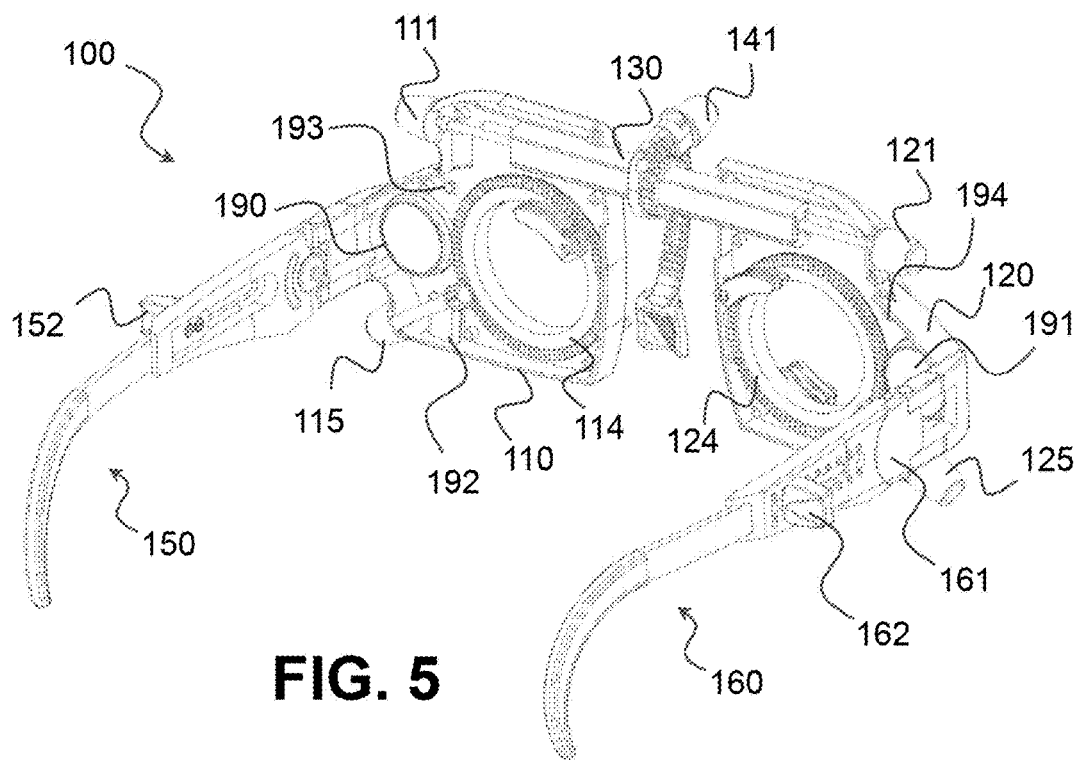
FIG. 5 is a rear perspective view showing an interior of the optical trial frame of FIG. 1.

FIGS. 1-5 show the left and right frames 110, 120 connected or coupled to respective left and right temples 150, 160. Each of the left and right temples 150, 160 may comprise a plurality of parts allowing a user to adjust their lengths and/or their relative positions (i.e., angular orientations) relative to the left and right frames 110, 120. Side angle adjustment portions 151, 161 may be provided on the left and right temples 150, 160 and pivotably mounted on the respective frames 110, 120. These adjustment portions 151, 161 may be rotated such that, in turn, an angular "tilt" of the lenses with respect to the line from the eye to the center of the aperture (the pantoscopic angle) is adjusted. Side length adjustment portions 152, 162 may also be provided to adjust the lengths of the temples 150, 160 to suit the location of the patient's ears. Although FIG. 5 shows a particular length adjustment mechanism, it will be apparent to those skilled in the art that any mechanism or arrangement suitable to adjust a length of a trial frame temple may be provided.

The left and right frames 110, 120 may further comprise or be connected to lens holders 112, 113, 122, 123 adapted to receive and retain lenses in use. As explained hereinabove, the trial frame 100 comprises means for allowing adjustment to accommodate, for example, the differing facial and interpupilar requirements of patients so that lenses may be positioned along the line-of-sight of the patient. In use, the orthoptists, optometrists or ophthalmologists may use lenses of different shapes or powers so as to determine the combination of ophthalmic lenses that will provide the BCVA for a patient. Once the most satisfactory lens power is determined and positioned in line-of-sight, the best visual acuity may be obtained by rotating the lens holders 112, 113, 122, 123. The lens holders 112, 113, 122, 123 are coupled to rings 114, 124 which are rotatably connected to the frames 110, 120. Operational elements 115, 125 which can be similar to the ones described previously may be provided to manually rotate the lens holders 112, 113, 122, 123 and/or the rings 114, 124 relative to the frames 110, 120. An angular or rotational displacement of the lens holders 112, 113, 122, 123 and/or the rings 114, 124 may therefore be detected and measured by the sensing means so as to determine positions of the lens holders 112, 113, 122, 123 and/or the rings 114, 124 relative to respective left and right frames 110, 120. The angular positions of the lens holders 112, 113, 122, 123 and/or the rings 114 can then be displayed on the one or more display units 170, 180. In some embodiments, the one or more display units 170, 180 may be configured to display one or more of the following: a lateral position of the left frame 110; a lateral position of the right frame 120; an interpupillary distance; a rotational position of the left lens holders 112, 113 and/or ring 114; and, a rotational position of the right lens holders 122, 123 and/or ring 124.

In some embodiments, the trial frame 100 may comprise light sources 193, 194 provided respectively into the left 110 and right 120 frames. For example, but not limited to, the light sources 193, 194 may comprise light-emitting diodes (LEDs) arranged and configured to illuminate the centre of the pupils. In use, the user would adjust the left and right frames 110, 120 and the left and right lens holders 112, 113, 122, 123 such that the centre of the lens holders 112, 113, 122, 123 is aligned with the corneal reflex. In turn, this will ease measurement of the interpupillary distance. The light sources 193, 194 (e.g., LEDs) may also be arranged and configured to illuminate the corneal apex. The corneal apex is usually hard to visualise as there is not enough light in the area between the frames and the cornea. Therefore, providing light sources 193, 194 into the left 110 and right 120 frames will also ease measurement of the back vertex distance that is to say the distance between the lenses (configured to be received into the lens holders 112, 113, 122, 123) and the corneal apex.

Figure 6:
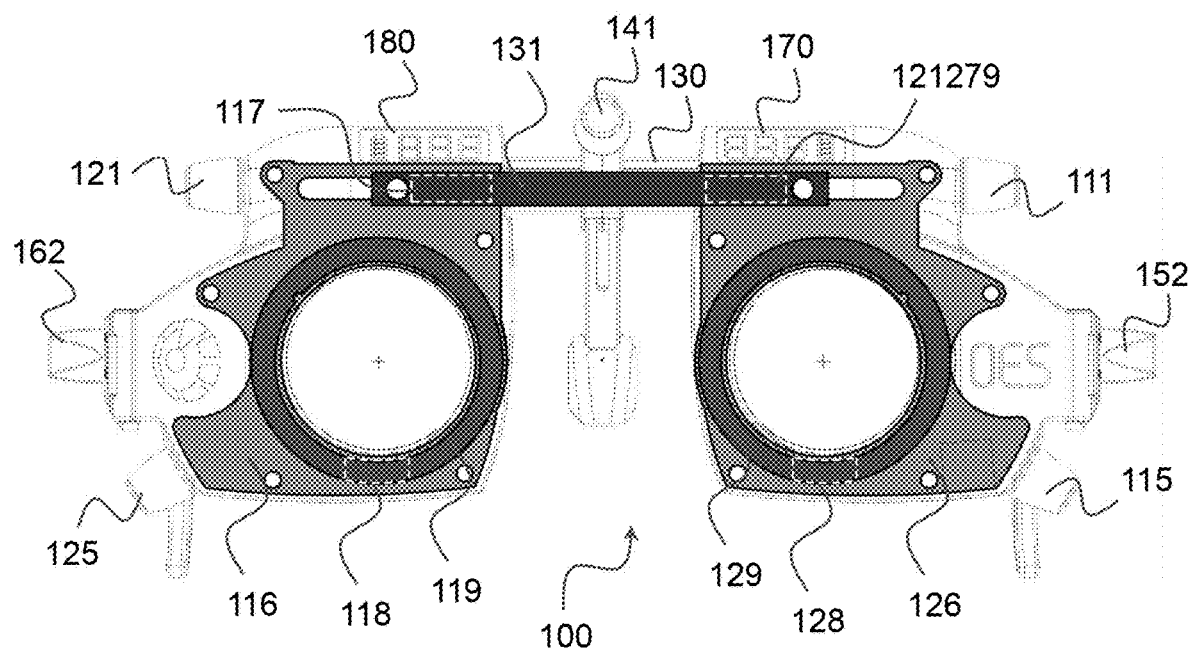
FIG. 6 is a rear view showing an interior of an optical trial frame constructed and operative with an embodiment of the invention.

Reference is now made to FIG. 6, which illustrates an interior of the trial frame showing sensing means constructed and operative in accordance with an embodiment of the present invention. FIG. 6 shows an arrangement of the trial frame 100 comprising printed circuit boards 116, 126 comprising at least one linear displacement or motion sensor 117, 127 and at least two rotational sensors 118, 128. The linear displacement or motion sensor 117, 127 is configured to detect and measure a linear motion of the frames 110, 120 relative to each other and/or relative to the bridge 130 such that a lateral position of the frames 110, 120 and/or an interpupillary distance can be determined. In addition, and/or alternatively, the rotational sensors 118, 128 are configured to detect and measure a rotational motion of the lens holders 112, 113, 122, 123 and/or the rings 114, 124 relative to the frames 110, 120 such that a rotational position of the lens holders 112, 113, 122, 123 and/or the rings 114, 124 can be determined.

In one embodiment, the linear 117, 127 and rotational 118, 128 sensors may be implemented as capacitive sensors. A capacitor may be formed when two overlapping conductive plates are separated by a small distance. When a voltage is applied across these conductive plates, an electric charge becomes present and is exchanged between the plates through a medium. In turn, an amount of electrical charge (i.e., capacitance) being transferred can be measured. When the conductive plates move relative to each other, a variation of the capacitance can be detected, measured and subsequently used as an indicator signal representative of the linear and/or rotational displacement. This signal may then be converted into a digital form, and a resulting linear or rotational displacement may be calculated by a computing device and/or any suitable processing circuitry.

The linear 117, 127 and rotational 118, 128 sensors may each comprise a capacitor formed by fixed and moving electrodes. The linear sensors 117, 127 may comprise a fixed electrode formed to the sensor PCB 131 so that an electrode surface of the electrode is coupled to and extends parallel to the bridge 130 (i.e., along the longitudinal axis of the bridge 130). When a target portion of the PCBs 116, 126 with an electrically conductive surface is mounted to the trial frame 100, a moving electrode is created thereby forming a capacitor. In use, the linear fixed and moving electrodes face toward each other without any direct physical contact. However, the moving electrode is making direct electrical contact with the fixed electrode such that an electrical charge provided by a power source (e.g., batteries 190, 191) under the control of a computing processing unit (CPU) or microprocessor can be exchanged. Because of the linear displacement between the fixed electrode and the moving electrode which are facing each other without physical contact, the linear sensors 117, 127 are able to measure the capacitance and/or variations in capacitance and transfer these measurements to the CPU unit or microprocessor. In turn, a lateral displacement of the left and right frames 110, 120 relative to the bridge 130 may be determined/calculated and then displayed on the display units 170, 180.

Similarly, the rotational sensors 118, 128 may comprise a fixed electrode formed to the PCB 116, 126 so that an electrode surface extends parallel to sensor PCBs 119, 129 coupled to each of the rings 114, 124. When target inner surfaces of the sensor PCBs 119, 129 with electrically conductive surfaces are mounted to the trial frame 100, moving electrodes are created thereby forming capacitors. In use, the rotational fixed and moving electrodes face toward each other without any direct physical contact. However, the moving electrodes are making direct electrical contact with the fixed electrodes such that an electrical charge provided by a power source (e.g., batteries 190, 191) under the control of a CPU unit or microprocessor can be exchanged. Because of the rotational displacement between the fixed and moving electrodes which are facing each other without physical contact, the rotational sensors 118, 128 are able to measure the capacitance and/or variations in capacitance and transfer these measurements to the CPU unit or microprocessor. In turn, a rotational displacement of the rings 114, 124 relative to the frames 110, 120 may be determined/calculated and then displayed on the display units 170, 180.

Figure 7:
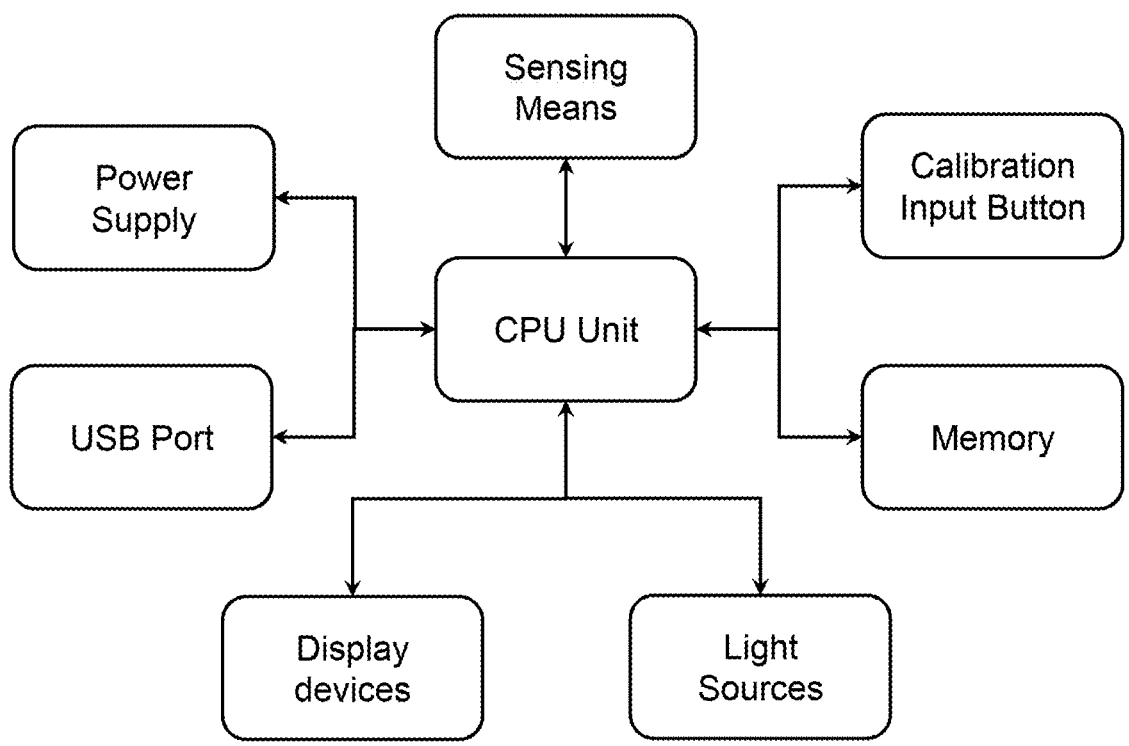
FIG. 7 is a simplified block diagram illustration showing components of an optical trial frame constructed and operative in accordance with embodiments of the invention.

Reference is now made to FIG. 7 which is a block diagram showing different elements of a trial frame, constructed and operative in accordance of embodiments of the invention. The trial frame 100 may comprise one or more power supplies, at least one Universal Serial Bus (USB) port, a computing processing unit (CPU), sensing means, calibration means, one or more display devices, a memory and any suitable circuitry allowing the different elements of the trial frame 100 to be powered and exchange data.

In one embodiment, power supplies may be provided on each frame. For example, in the embodiments depicted in FIGS. 1-5, power supplies are provided adjacent the PCBs 116, 126 and the rings 114, 124. However, those skilled in the art will appreciate that these power supplies 190, 191 may be placed at any convenient and/or any suitable location on the trial frame 100 as long as adequate circuitry is provided to connect them to the other elements. In use, the power supplies are configured to provide power to the different elements of the trial frame 100 such as, but not limited to, a microprocessor and/or the CPU unit, the sensing means and the display devices, as instructed by the CPU unit. The power supplies may be controlled to operate in run and standby modes. In run mode, the power supplies are configured to operate for at least one hour without requiring to be recharged. In standby mode, the power supplies are configured to operate for at least one day without any recharge. In addition, the power supplies are selected such that a target minimum lifetime before full replacement is of at least one year. The power supplies may be recharged at any time via the USB port connectable in use to a power source.

The CPU unit may be any suitable processing unit or units such as, for example but not limited to, a single chip microprocessor circuit, operative and programmed to control the timing, mode, computation and display functions of the trial frame 100. FIG. 7 shows the different elements of the trial frame 100 connected to and/or in communication with the CPU unit. For example, the CPU unit may be in electrical connection and/or data communication with at least one or more of: at least one power supply (e.g., power supplies 190, 191), the sensing means (e.g., sensor PCBs 116, 126, 117, 118, 127, 128, 119, 129, and 131), a memory, one or more display devices (e.g., display units 170, 180), a calibration input button, the USB port (e.g., port 192), and light sources (e.g., light sources/LEDs 193, 194). In use, the CPU unit is configured to control the different elements of the trial frame 100 using memory to perform one or more of the following tasks or processes:

- Optimise power management and power distribution across the different elements;
- Optimise power supplies charging;
- Manage standby and run modes of the power supplies;
- Optimise brightness and power consumption of the display devices;
- Control and monitor electrical charges sent to and used by the sensing means;
- Receive signals and/or measurements from the sensing means;
- Compute and/or calculate the linear displacements of the left and right frames and/or the interpupillary distance as well as the speed and angular rotations of the rings based on signals/measurements received from the sensing means;
- Receive inputs from the calibration input button and reset and/or update the measurements and/or calculations listed hereinabove; and,
- Exchange data with external devices, including receiving and updating a firmware and/or executable instructions stored in memory.

Memory may be of any suitable type and typically comprises random access memory (RAM), read only memory (ROM), flash memory, integrated circuits, and/or other memory components. Memory typically stores computer-executable instructions to be executed by CPU unit and/or data which is manipulated by CPU unit for implementing functionality in accordance with an embodiment.

The USB port may be provided at any suitable location on the trial frame 100 as long as a power and/or data cable can be provided and plugged into it. The USB port may be configured to receive a power cable in order to recharge the power supplies. In addition, or alternatively, the USB port may be configured to receive a data cable to exchange data. For example, data relevant to some components of the trial frame 100 and/or data sensed by the sensing means can be transmitted to an external device for further processing. In another example, an external device may be programmed to update the data and/or executable instructions (e.g., firmware) stored in the memory. It will be apparent to those skilled in the art that a single cable operative to recharge the power supplies and exchange data may be used.

The sensing means may be any suitable sensing means allowing detection and measurement of: the linear displacement of the frames relative to each other and/or relative to the bridge; the interpupillary distance; and, the rotational displacement of the lens holders or rings relative to the frames. In one example (depicted in FIGS. 1-5), the sensing means are implemented as capacitive sensing means. The sensing means may comprise capacitive touch sensors each having multiple internal capacitors with one side of each capacitor representing an input sensor and the other side (i.e., common side shared with all capacitors) representing an excitation signal. When an object touches any of the input sensor, a change of capacitance is created. This capacitance change can be expressed in voltages and then be converted digitally into a 16-bit number using a Capacitance-to-Digital Convertor (CDC) which is built into a capacitive touch sensor chip, the CDC having multiple conversion stages based on the type of sensor required. In this example, the sensor works as a slider where each sensor track is connected to each capacitive sensor input channel. When the linear or rotational sensor starts moving, the CDC begins to generate digitally converted numbers or outputs that represent the change in capacitance. These converted numbers or outputs may be pre-calibrated using, for example, but not limited to, 0.2 mm step measurements. These converted numbers or outputs may then be stored in the memory against each measurement step thereby forming a lookup table in which the index of the table represents the step, and the content of each item represents the converted number or output. The CPU unit may scan the converted numbers or outputs at each of the track trying to find a match against the stored numbers in the lookup table. If and/or when a match is found at a specific track, the CPU unit may be configured to convert it into a distance (e.g., in mm) by reading the index in the lookup table. In this example, the conversion performed by the CPU unit to calculate and/or compute the different displacements is as follows:

$$\text{Linear Distance} = \text{Lookup Table Index} \times 0.2 \text{ mm; and,}$$

$$\text{Rotational Angle} = \frac{\text{Lookup Table Index} \times 0.2 \text{ mm}}{2 \times \pi \times R}$$

where, R is the radius that is known in advance. In addition, the converter numbers or outputs may be normalized to account for/filter noise.

The sensing means may be configured to detect and measure: an angular displacement with a minimum resolution of 1 degree; a linear displacement with a minimum resolution of 0.5 degree; a linear displacement with a maximum speed of 5 millimeters per second; and, an angular displacement with a maximum speed of 30 degrees per second.

In one embodiment shown in FIGS. 1-4 and 6, two display devices (e.g., display units 170 and 180) are provided on the trial frame 100. Display device 170 may be provided on the left frame 110 adjacent the bridge 130. Similarly, display device 180 may be provided on the right frame 120 adjacent the bridge 130 but on the opposite side of the nose pad 140. Although two display devices 170, 180 are illustrated, those skilled in the art will appreciate that any suitable number of display devices can be provided (e.g., a single display unit or more than two). Similarly, although the display devices 170, 180 are provided on upper portions of the frames 110, 120, it will be apparent that they can be provided at any suitable location on the trial frame 100 as long as appropriate circuitry is provided for connection to the CPU, the power supplies 190, 191, and any other elements of the trial frame 100. The display units 170, 180 may be configured to display one or more of: a lateral position of the left frame 110; a lateral position of the right frame 120; an interpupillary distance; a rotational position of the left ring 114 or left lens holders 112, 113; and, a rotational position of the right ring 124 or right lens holders 122, 123. In one example, values may be displayed with zero decimal places, in full degree increments. In another example, the linear displacement values or interpupillary distance may be displayed with one decimal place, in half a millimeter increments. In a further example, the display units 170, 180 may be configured to display the linear and angular measurement values simultaneously allowing an operator to read the measurements from a distance of 600 mm in a dark room. The display devices may further be configured to indicate to the operator when a recharge is required. For example, the display devices 170, 180 may be configured to display a visual indication indicating that the one or more power supplies 190, 191 are low, e.g., under a predetermined power threshold.

In another embodiment, the trial frame 100 may not include any display units but rather the data and/or measurements may be transmitted to an external device adapted to process the data/measurements and/or an external display unit adapted to display the measurements or calculated values. For example, the data/measurements can be transmitted to the external device/display via a cable plugged to the USB port 192 under the control of the CPU. In addition, or alternatively, a wireless transmitter can be incorporated to the trial frame 100 to allow wireless transmission of the data/measurements to the external device/display.

Many advantages of the different embodiments described hereinabove will be apparent to those skilled in the art. For example, the use of low power capacitive sensing means allows accurate detection and measurement of the displacements of the different elements of the trial frame. Use of display units allows easy and direct readings of the different measured or calculated values alleviating the need for orthoptists, optometrists or ophthalmologists to read printed scales and perform any additional calculations. The configuration and arrangement of the different elements also provide for a light trial frame thereby improving portability and reuse.

Still other objects, features, and attendant advantages of the present invention will become apparent to those skilled in the art from a reading of the above detailed description of embodiments constructed in accordance therewith, taken in conjunction with the accompanying drawings.

While the invention has been described in connection with a preferred embodiment, it is not intended to limit the scope of the invention to the particular form set forth, but on the contrary, it is intended to cover such alternatives, modifications, and equivalents as may be included within the spirit and scope of the invention as defined by the appended claims.

It will be appreciated by those skilled in the art that the present invention can be embodied in other specific forms without departing from the spirit or essential characteristics thereof. The presently disclosed embodiments are therefore considered in all respects to be illustrative and not restricted. The scope of the invention described by the foregoing includes all changes that come within the meaning, range and equivalence thereof and is intended to be embraced therein.

What is claim is:

1. A trial frame comprising:
   left and right frames extending in the left and right directions respectively;
   a bridge located between and connected to the left and right frames such that the left and right frames can move relative to each other along a longitudinal axis of the bridge;
   left and right temples connected to the respective left and right frames;
   left and right lens holders rotatably coupled to the left and right frames respectively and configured to receive and retain lenses in use; and,
   capacitive sensing means configured to detect and measure at least one of: a lateral position of one of the frames; and, a rotational position of one of the lens holders.

2. The trial frame of claim 1, wherein the capacitive sensing means are configured to detect and measure linear motions of the left and right frames and/or rotational motions of the left and right lens holders.

3. The trial frame of claim 2, wherein the capacitive sensing means comprises a first capacitive sensor configured to detect and measure a linear motion of at least one of the frames relative to the other and/or relative to the trial frame, the first capacitive sensor comprising:
   a fixed electrode coupled to one of the frames; and,
   a linear moving electrode configured to be electrically connected to the fixed electrode.

4. The trial frame of claim 3, the first capacitive sensor is configured to detect and measure the linear motion with a minimum resolution of about, 0.5 degree; and/or a maximum linear motion of about 5 millimeters per second.

5. The trial frame of claim 3, wherein the fixed electrode is formed as a conductive surface coupled to a printed circuit board; and/or the linear moving electrode is formed by a conductive surface of the bridge.

6. The trial frame of claim 2, wherein the capacitive sensing means comprises one or more second capacitive sensors configured to detect and measure a rotational motion of lens holders relative to their respective frame, each of the one or more second capacitive sensors comprising:
   a fixed electrode coupled to one of the frames; and,
   a rotational moving electrode configured to be electrically connected to the fixed electrode.

7. The trial frame of claim 6, wherein the second capacitive sensor is configured to detect and measure a rotational motion with a minimum resolution of about 1 degree; and/or a maximum rotational motion of about 30 degrees per second.

8. The trial frame of claim 6, wherein the fixed electrode is formed as a conductive surface coupled to a printed circuit board; and/or the rotational moving electrode is formed by a conductive surface coupled to the lens holders.

9. The trial frame of claim 1, wherein the capacitive sensing means are configured to detect and measure a capacitance and/or a variation of capacitance when provided with an electrical charge.

10. The trial frame of claim 1, further comprising light sources arranged on the left and right frames and configured to illuminate in use a corneal apex of a user and/or a centre of pupils of a user.

11. The trial frame of claim 10, wherein the light sources comprise light-emitting diodes.

12. The trial frame of claim 1, further comprising a computing processing unit (CPU) configured to receive the measured lateral and rotational positions from the sensing means and to process the lateral positions to compute an interpupillary distance.

13. The trial frame of claim 12, wherein the trial frame is associated with one or more display units configured to display at least one of: the measured lateral position of at least one of the frames; the measured rotational position of one of at least one of the lens holders; and, the computed interpupillary distance.

14. The trial frame of claim 13, wherein at least one of the one or more display units is integral with the left or right frame; and/or at least one of the one or more display units is external to the trial frame.

15. The trial frame of claim 14, further comprising a transmitter configured to transmit the measured positions and/or the computed interpupillary distance to an external device and/or the at least one external display device.

16. The trial frame of claim 1, further comprising one or more power supplies configured to provide power to at least the sensing means.

17. The trial frame of claim 16, wherein the one or more power supplies are further configured to provide power: to a CPU configured to receive the measured lateral and rotational positions from the sensing means and to process the lateral positions to compute an interpupillary distance; and/or one or more display units configured to display at least one of: the measured lateral position of at least one of the frames; the measured rotational position of one of at least one of the lens holders; and, the computed interpupillary distance.

18. The trial frame of claim 1, further comprising a port configured to connect the trial frame to an external device wherein the external device is a power source configured to recharge one or more power supplies provided on the trial frame when connected to the trial frame.

19. The trial frame of claim 18, further comprising a memory configured to store computer-executable instructions and wherein the external device is configured to update the computer-executable instructions stored in the memory when connected to the trial frame.

20. The trial frame of claim 1, further comprising a port configured to connect the trial frame to an external device, wherein the external device is configured to exchange data with the sensing means and/or a CPU when connected to the trial frame.

* * * * *